United States Patent
Snelling et al.

(10) Patent No.: US 6,181,419 B1
(45) Date of Patent: Jan. 30, 2001

(54) METHOD AND APPARATUS FOR APPLYING LASER INDUCED INCANDESCENCE FOR THE DETERMINATION OF PARTICULATE MEASUREMENTS

(75) Inventors: David R. Snelling, Almonte; Gregory J. Smallwood, Orleans; Ömer L. Gülder, Ottawa, all of (CA)

(73) Assignee: National Research Council of Canada, Ottawa (CA)

(*) Notice: Under 35 U.S.C. 154(b), the term of this patent shall be extended for 0 days.

(21) Appl. No.: 09/316,382

(22) Filed: May 21, 1999

Related U.S. Application Data

(60) Provisional application No. 60/086,506, filed on May 22, 1998.

(51) Int. Cl.$^7$ .................................................. G01N 15/02
(52) U.S. Cl. ........................ 356/335; 356/336; 250/575
(58) Field of Search ..................................... 356/335, 336, 356/338, 339, 342, 343, 347, 348, 43, 46, 47, 315; 372/69; 250/554, 575, 574

(56) References Cited

U.S. PATENT DOCUMENTS

| | | | |
|---|---|---|---|
| 4,429,995 | * | 2/1984 | Goulas .................................. 356/343 |
| 5,180,921 | * | 1/1993 | Moreau et al. ........................ 250/554 |
| 5,285,467 | * | 2/1994 | Scheps ................................... 372/69 |
| 5,920,388 | * | 7/1999 | Sandberg et al. ..................... 356/315 |

OTHER PUBLICATIONS

WO 97/303335 International Appln PCT/EP97/00638, Method for the in situ characterization of primary particles and particle aggregates Aug. 21, 1997.

Soot Diagnostics Using Laser–induced Incandenscence in Flames and Exhaust Flows R.T. Wainner; J.M. Seitzman Georgia Institute of Technology American Institute of Aeronautics and Astronautics, AIAA–99–0640 1999.

* cited by examiner

Primary Examiner—Hoa Q. Pham
Assistant Examiner—Sang H. Nguyen
(74) Attorney, Agent, or Firm—Freedman & Associates

(57) ABSTRACT

The present invention relates to a method and apparatus for applying laser induced incandescence (LII) to determine a primary particle size of submicron sized particles. The present invention has found that in addition to volume fraction information, particle size can be determined using LII due to the fact that transient cooling is dependent on the diameter of the particle. The ratio of a prompt and a second time integrated measurement from the same laser pulse has been found to be a function of the particle size. A modeling process involves a solution of the differential equations describing the heat/energy transfer of the particle and surrounding gas, including parameters to describe vaporization, heat transfer to the medium, particle heating etc. The solution gives temperature and diameter values for the particles over time. These values are then converted to radiation values using Planck's equation. Thus the technique in accordance with the invention is able to provide a more accurate particle measurement than previous LII techniques, particularly where time averaging is not possible and size measurements must be obtained from a single laser pulse. Simultaneously a particle volume fraction can be obtained in accordance with the invention. Calibration is needed to obtain a quantified volume fraction measurement. In a further embodiment of the present invention, a technique for providing absolute intensity calibration is included in the method.

25 Claims, 10 Drawing Sheets

METHOD AND APPARATUS FOR APPLYING LASER INDUCED INCANDESCENCE FOR THE DETERMINATION OF PARTICULATE MEASUREMENTS

This application claims benefit of Provisional Application Ser. No. 60/086,506, filed May 22, 1998.

FIELD OF THE INVENTION

The present invention relates to a method and apparatus for the determination of particle sizes and volume fraction of submicron sized particles, such as soot, over a wide range of particle concentrations with high temporal and spatial resolution.

BACKGROUND OF THE INVENTION

The presence of particulate matter, such as soot particles, in the environment has brought about an increased interest in the development of methods and devices for the determination of particulate concentration. Soot in particular has been the subject of study for measurement. However, all small particles pose an important area of interest and concern, particularly for environmental and health reasons. The emission of soot from engines, power generation facilities, incinerators, or furnaces, for example, represents a loss of useful energy and further is a serious environmental pollutant and a health risk. However, the presence of soot in flames can also have positive effects. For example, the energy transfer from a combustion process is largely facilitated by the radiative heat transfer from soot. Thus, to understand soot formation and develop control strategies for soot emission or formation, measurements of soot concentrations are necessary. Laser Induced Incandescence (LII) is a good diagnostic tool for measurements of particulates as the LII signal is proportional to particle volume fraction.

The measurement of soot particle concentrations has been greatly improved by the development of Laser Induced Incandescence (LII), which can provide concentration information with high temporal and spatial resolution. Previous techniques could not detect small concentrations and could not provide accurate time responsive information regarding soot formation.

LII exposes a volume of gas containing refractory particles, that is particles capable of absorbing laser light energy with an evaporation temperature sufficiently high to produce measurable incandescence, to a pulsed focused high-intensity laser light. The particles absorb laser energy heating to temperatures far above the surrounding gas. At these elevated temperatures (about 4000–4500 K in the case of soot) the particles incandesce strongly throughout the visible and near infrared region of the spectrum. The maximum temperature is controlled by the point at which evaporation becomes the predominant heat loss mechanism. Any further increase in laser light energy then tends to result in an increase in the evaporation rate rather than an increase in particle temperature. In accordance with Planck's radiation law, the radiative emission at these elevated temperatures increases in intensity and shifts to blue wavelengths. Thus the LII signal is readily isolated from any natural flame emission. Because of the rapid time scale and good spatial resolution, as well as its large dynamic range, LII is well suited as an optical diagnostic to measure soot volume fraction in turbulent and time varying combustion devices.

In an application by Alfred Leipertz et al WO 97/30335 published Aug. 21, 1997 a laser-induced incandescence technique is described for determining a primary particle size. The method taught by Leipertz includes the measurement of the incandescence at two discrete points in time after the laser light pulse, from which a ratio is generated to calculate the particle size according to a mathematical model. However, this method has been shown to be prone to inaccuracies. Leipertz samples the two measurements at a point of decay where he assumes a linear change. This is not possible until significant cooling has occurred and most of the signal has passed. Thus the signals measured by Leipertz are very weak and are highly influenced by noise. And the assumption of a linear decay in the incandescence is not accurate adding to the inaccuracy of the system. The ambient temperature of the surrounding gas is also significant to modeling the decay, and is not considered by Leipertz. Laser fluence over the volume measured is also critical to the subsequent decay. It is critical for accuracy to know the energy density profile over the volume. This factor is assumed without verification by Leipertz's technique. Further error is introduced by the detection method which uses broad band detectors to measure the signal. Since the detected incandescence intensity is used as an indication of temperature, and the intensity varies in accordance with temperature and wavelength, a sample over a broad band of wavelengths greatly complicates and obscures accurate measurement. The Leipertz technique, as a result of these introduced errors, does not provide a good measurement of particle size.

Attempts to characterize particle size are also disclosed in a paper "Soot diagnostics using laser-induced incandescence in flames and exhaust flows" by R. T. Wainner and J. M. Seitzman published in 1999, by the American Institute of Aeronautics and Astronautics. This article reviews a method to determine particle size by measuring the peak temperature attained (pyrometry) by LII. However, the study found that the temperature of different-sized particles can be identical and thus temperature measurement at the peak is not sufficient to determine particle size.

Thus an accurate method for particle size is still needed. In addition, the known LII techniques as currently practiced are not practical for use in diagnostic and emissions testing of combustion engines. A compact and portable device is needed for practical use. Current methods for measuring diesel particulates are the Bosch Smoke Number and the direct mass sampling. In the Bosch Smoke Number method particulates are collected on filter paper from a portion of the exhaust stream and the light reflection from the collected sample is measured. This is compared against a calibration chart to determine the mass flow. Since sufficient sample material must be collected over time, this method requires a long period for sample collection and has a poor time and spatial resolution. Thus this method cannot provide diagnostic information about the formation of particles in the combustion cycle. The direct mass sampling method is the official method of the EPA and measures the mass of soot from a difference of the mass of the soot on a filter and subtracting the mass of the filter. This method, however, has a limited accuracy, particularly for low emission vehicles. Both methods suffer a loss in accuracy when the source produces lower emissions, and require significantly longer testing for low emission combustors.

It is desired to accurately measure the primary particle size of particles with high temporal and spatial resolution. Small particles, in particular, have been found to present significant health concerns. However, using traditional methods particles under 500 nm size are not differentiated, and existing LII techniques for determining small particle size are not satisfactory. Advantageously, the LII technique can provide instantaneous point measurements of soot concentration in turbulent flames such as are found in most practical combustors, including gasoline engines, Diesel engines, gas turbine engines, furnaces, and boilers.

It is desired to provide a LII method and apparatus suitable for both more accurately determining particle volume fraction and for determining primary particle diameter which is accurate, compact, transportable and suitable for use in situ for practical applications such as turbulent flame combustion devices, exhaust flow and ambient measurements.

SUMMARY OF THE INVENTION

The present invention has found that in addition to volume fraction information, particle size can be determined using LII due to the fact that transient cooling is dependent on the diameter of the particle. A modeling process involves a solution of the differential equations describing the heat/energy transfer of the particle and surrounding gas, including parameters to describe vaporization, heat transfer to the medium, particle heating etc. The solution gives temperature and diameter values for the particles over time. These values are then converted to radiation values using, for example, Planck's equation. The ratio of a first substantially instantaneous prompt measurement and a second time integrated measurement from the same laser pulse has been found to be a function of the particle size. Thus the technique in accordance with the invention is able to provide a more accurate particle measurement than previous LII techniques, particularly where time averaging is not possible and size measurements must be obtained from a single laser light beam pulse. Simultaneously a particle volume fraction can be obtained in accordance with the invention. Calibration is needed to obtain a quantified volume fraction measurement. In a further embodiment of the present invention, a technique for providing absolute intensity calibration is included in the method.

In accordance with the invention there is provided a method for determining an average particle size of one or more particles in a defined volume of gas comprising the steps of:

exposing the volume of gas to a laser light beam pulse to cause the one or more particles to incandesce;

obtaining a measurement of a prompt signal of incandescence intensity within a period of substantially unchanged intensity after the laser pulse with a photodetector means;

obtaining a measurement of a time integrated signal of incandescence intensity over a duration of time after the laser pulse with a photodetector means;

calculating a ratio of the prompt and integrated signals for application to a mathematical model representing the heating and cooling of the one or more particles and the type of particle; and determining the average particle size in dependence upon the ratio and the model.

In accordance with the invention the method further includes a method of simultaneously determining a particle volume fraction within the defined volume comprising the additional steps of:

incorporating the measurement of one of the prompt signal or of the time integrated signal or a time dependent signal of incandesence intensity into the mathematical model representing the heating and cooling of the one or more particles and the type of particle;

calibrating a signal intensity to quantify the measurement; and calculating the particle volume fraction.

In accordance with a further embodiment of the invention there is provided an apparatus for determining an average particle size of one or more particles in a defined volume of gas in a laser induced incandescence system comprising:

a laser for generating a pulsed light beam into the defined volume of gas for causing the one or more particles to incandesce;

at least one photodetector for detecting a prompt signal within a period of substantially unchanged incandescence intensity and for detecting a time integrated signal over a duration of time including a major portion of a total incandescence intensity;

processing means for calculating a ratio of the prompt signal and the time integrated signal and applying the ratio to a mathematical model representing the heating and cooling of the one or more particles and the type of particle to determine the average particle size.

In accordance with the present invention the apparatus further includes calibration means adapted for quantifying a particle volume fraction measurement wherein the calibration means comprises an extended source of known radiance having a known brightness temperature for calibrating the at least one photodetector to quantify its sensitivity.

Advantageously, the method in accordance with the present invention provides a more accurate diameter measurement of very small particles.

It is a significant advantage that the technique can provide accurate measurements with high temporal and spatial resolution from a single laser light pulse, even for low particle concentrations. This is in part because sampling the maximum intensity incandescence signal and the time integrated signal obtains strong incandescence signal information, providing a good signal to noise ratio.

A further advantage is that the apparatus in accordance with the present invention adapts the LII technique for in situ application, particularly with the convenience of absolute intensity measurements without the need for an additional calibration setup Additional advantages will be understood to persons of skill in the art from the detailed description of preferred embodiments, by way of example only, with reference to the following figures:

BRIEF DESCRIPTION OF THE DRAWINGS

Like numerals are used throughout to indicate like elements.

DETAILED DESCRIPTION OF PREFERRED EMBODIMENTS

Figure 1:
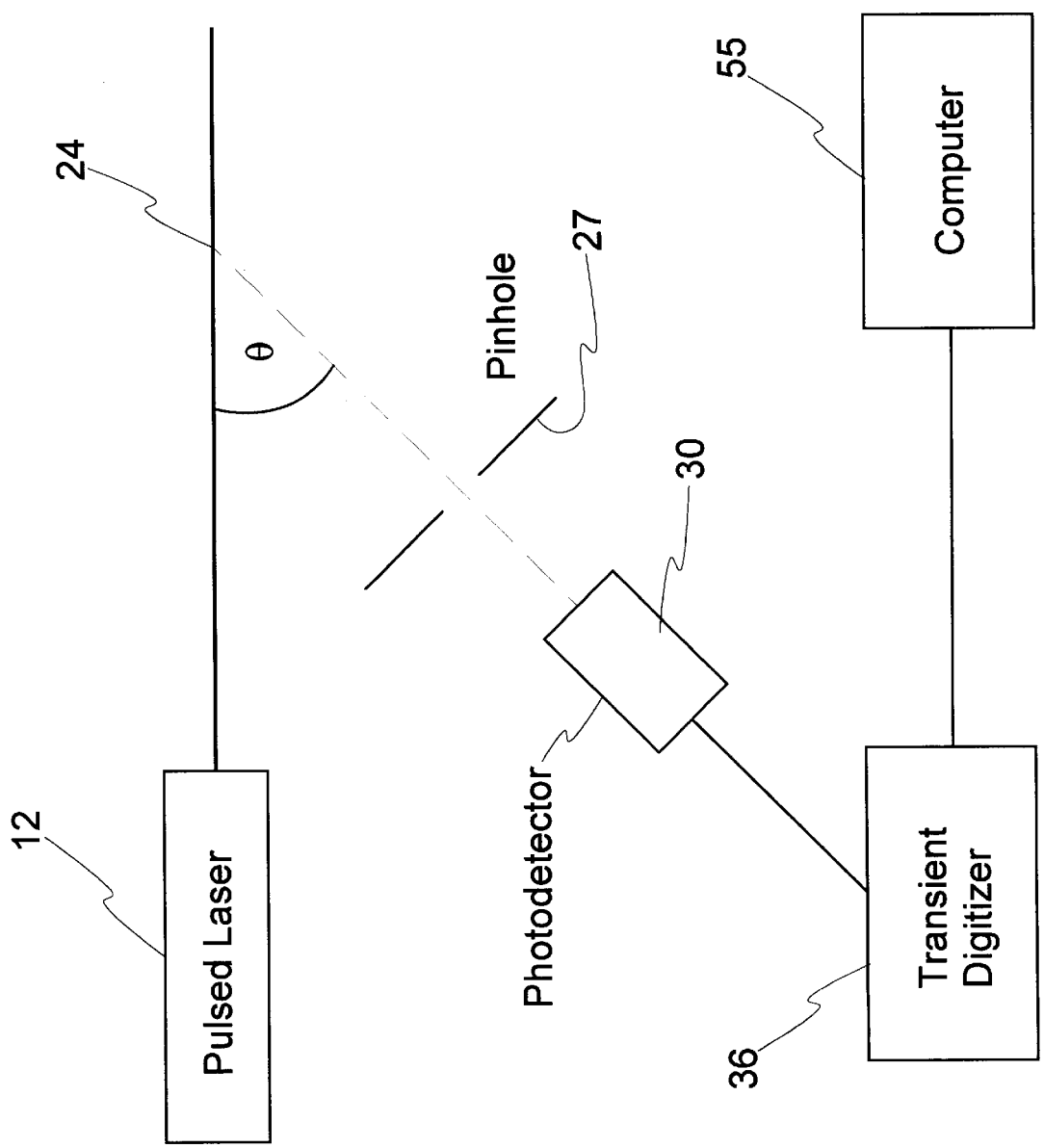
FIG. 1 is a schematic illustration of the basic LII apparatus.

The LII method in accordance with the present invention is introduced with reference to FIG. 1. A pulsed laser 12, capable of providing a beam with a light energy density sufficient to reach the particle evaporation temperature, is passed through the medium in which a measurement is desired. A photodetector 30, located at any arbitrary angle (θ) to the laser light beam, detects the radiation produced by interaction between the laser beam and particles contained in the medium. The measurement volume 24 is defined by the intersection of the field of view of the photodetector 30 and the path of the laser light beam. The measurement volume 24 can be further defined by use of focusing lenses for the laser light beam, collection lenses for the photodetector 30, or use of an aperture 27 restricting light to the detector 30. The signal from the detector 30 may be recorded by a transient digitizer 36, for further processing by the computer 55, or by a gated integrator 40 or other suitable means. A minimum of two photodetectors 30 are needed for instantaneous determination of the signal ratio, though both signals can be obtained from a single photodetector 30 and a transient digitizer 36 with further processing.

Figure 2:
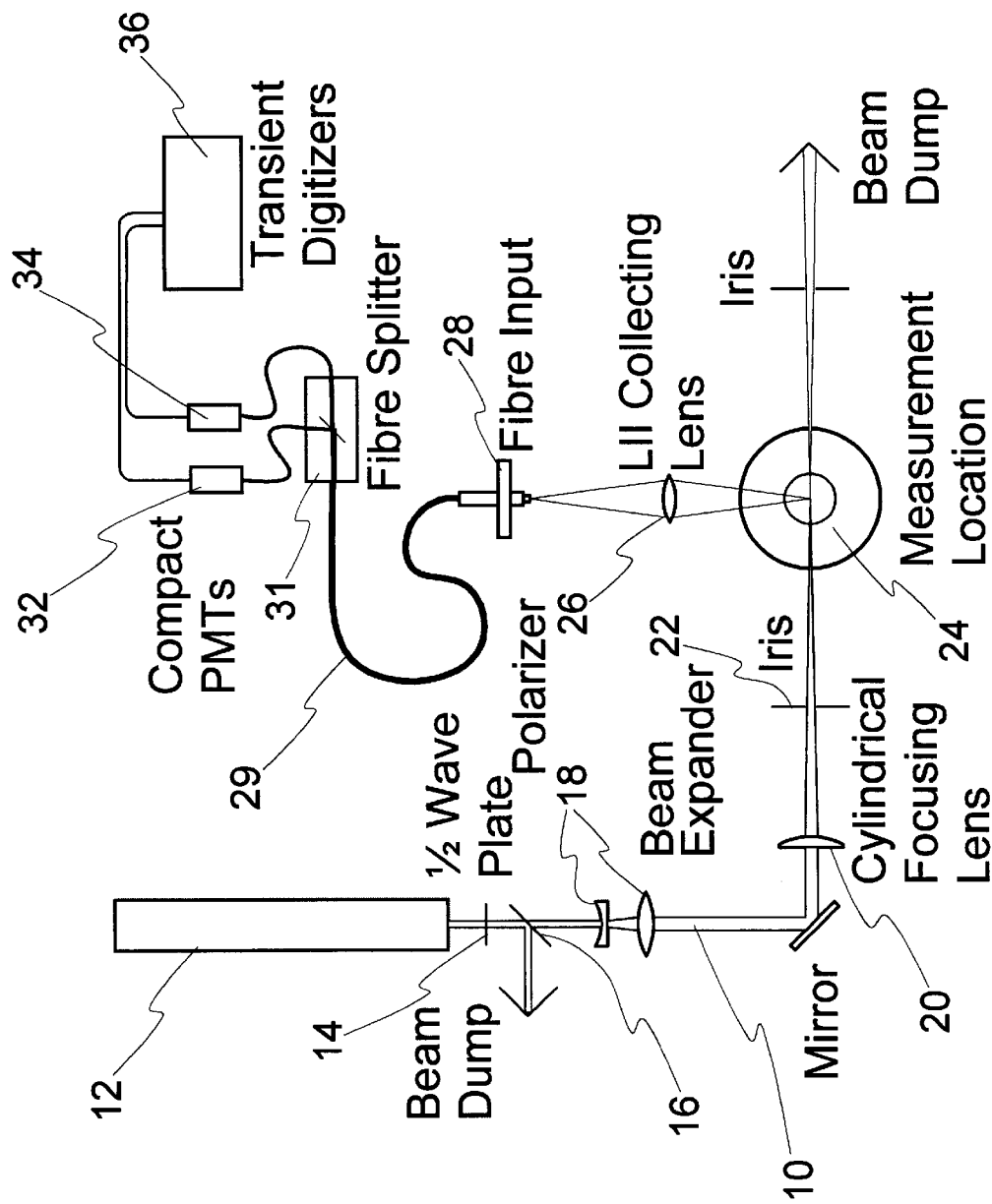
FIG. 2 is a schematic illustration of a preferred embodiment of the apparatus employing optical fiber coupling of the detected incandescence signal.
Figure 9:
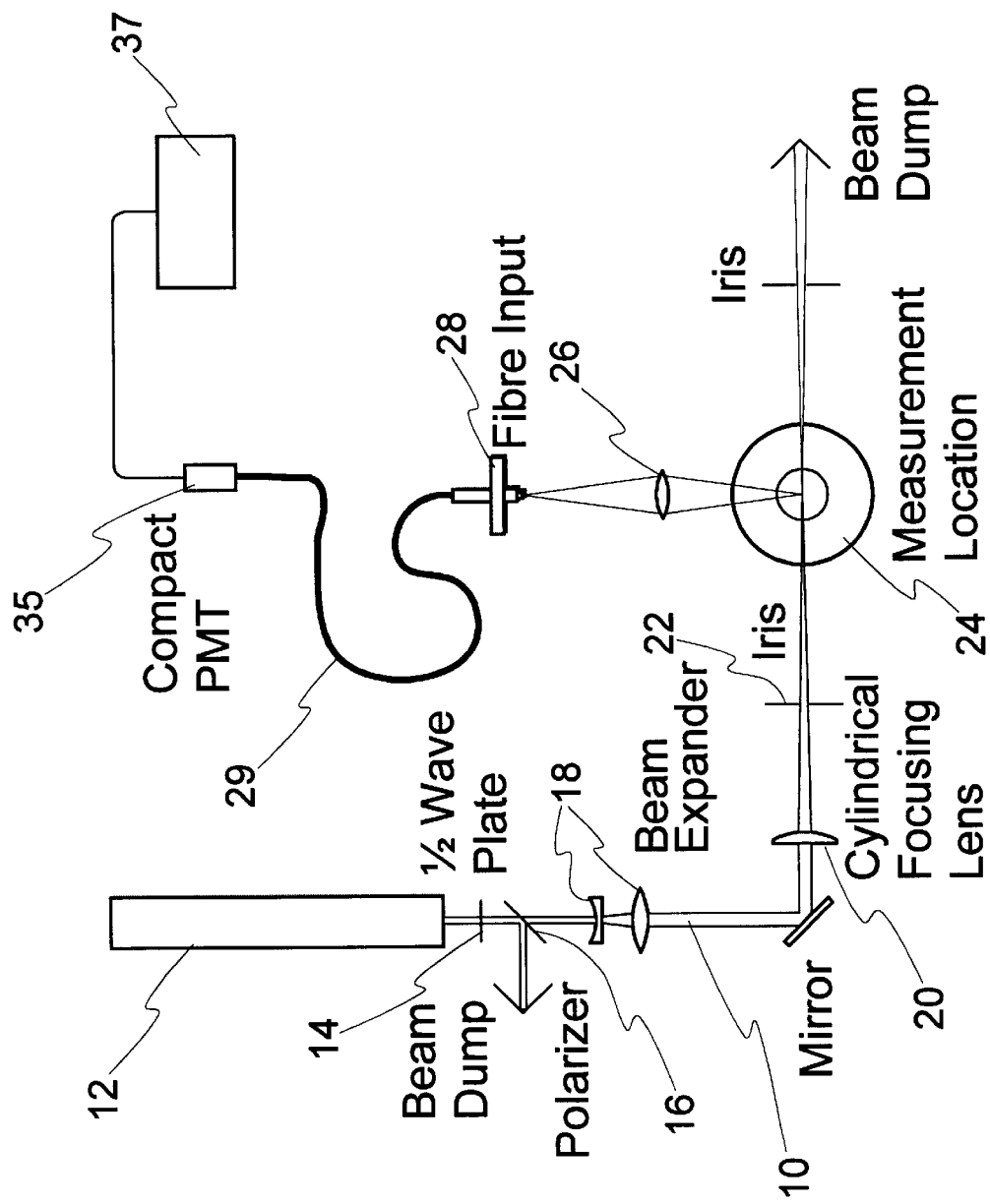
FIG. 9 is a schematic illustration of a further preferred embodiment of the apparatus employing optical fiber coupling of the detected signal having a single photodetector; and, FIG. 10 shows an optical schematic for the absolute intensity calibration.

A preferred embodiment of an apparatus in accordance with the present invention is illustrated in FIG. 2. The laser 12 directs a pulsed light beam 10 through a half wave plate 14 and polarizer 16 to control the laser energy. The beam 10 is then shaped through a beam expander lens system 18 and a focusing lens 20 for forming the beam 10 to a laser sheet. The laser sheet passes through an iris 22 to remove any scatter light or halo effects before passing through the measurement location 24. A collecting lens 26 directed toward the measurement location 24 perpendicular to the beam for maximum spatial resolution, collects and focuses the incandescent radiation generated by the laser light pulse into an optical fiber input 28, matching the numeric aperture of the fiber 29. In this case the measurement volume is determined by the intersection of the path of the laser light beam 10 and the field of view of the fiber input 28 from the laser sheet. The signal is then conveyed by the fiber 29 to an optical splitter 31 where the beam is collimated. An optical element splits the collimated beam into two or more parts, which are focused into output fibers 29 whose outputs terminate at the photomultipliers 32, 34. The optical splitter 31 can either divide the input signal beam into different light wavelength bands, or provide outputs of divided intensity where all of the wavelengths are present. Optionally, optical interference filters can be inserted before the final focusing lens to further select the light wavelength range provided to each of the photodetectors. A first detector 32 is a photomultiplier for detecting a prompt signal, and a second detector 34 is a photomultiplier connected to a charge-coupled amplifier (CCA) for collecting a time integrated signal simultaneously with the prompt signal. A digital integrator may be used to detect the time integrated signal. The CCA device is an economical detector and is preferred for this application, because the noise level is low relative to the accumulated signal. Alternatively, in place of the CCA one or more transient digitizers 36 receive the signals as a digital integrator for converting the analog signals for digital processing in the computer 55. A single transient digitizer 36 can be used to collect both prompt and integrated incandescence signal data, without the need for multiple detectors and splitters, as shown in FIG. 9.

Figure 3:
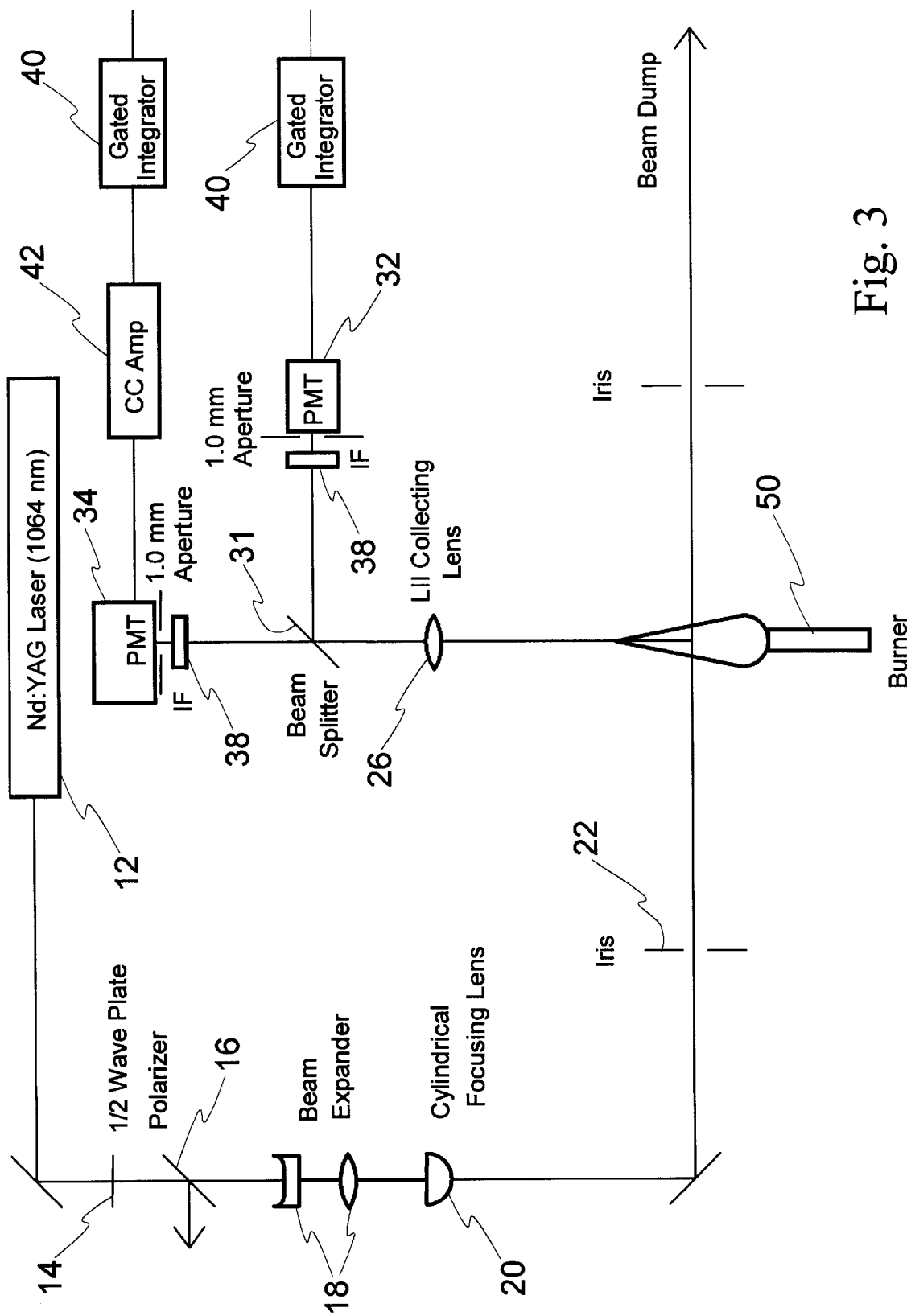
FIG. 3 is a schematic illustration of an additional preferred embodiment of the apparatus.

Referring to FIGS. 2 and 3, the method in accordance with the invention directs a pulsed focused light beam from the laser 12 to provide a substantially instant energy source (approximately 10 ns duration) to a volume containing the particles 24. Several mJ of energy are sufficient to rapidly heat the particles in the laser beam 10 to their evaporation temperature (approximately 4500K in the case of soot). At this temperature the particles radiate incandescence as they cool back to ambient temperature, the ambient temperature typically being 1500–2000K in combustion systems, and much lower in engine exhausts and ambient environments. The incandescence signal is collected and imaged to a pair of detectors 32, 34. The first detector 32 detects a prompt signal measurement of approximately 25 ns substantially at or near the peak incandescence intensity after the laser light pulse. The second detector 34 simultaneously measures a time integrated signal over a period of approximately 1 ms following the laser pulse through a charge-coupled amplifier 42 and a time gated integrator 40 or a simple sample-and-hold circuit (not shown). The prompt and integrated signals provide a measurement of peak light intensity and total light intensity over time as the particles cool and the heat transfers to the surrounding gas.

Figure 4:
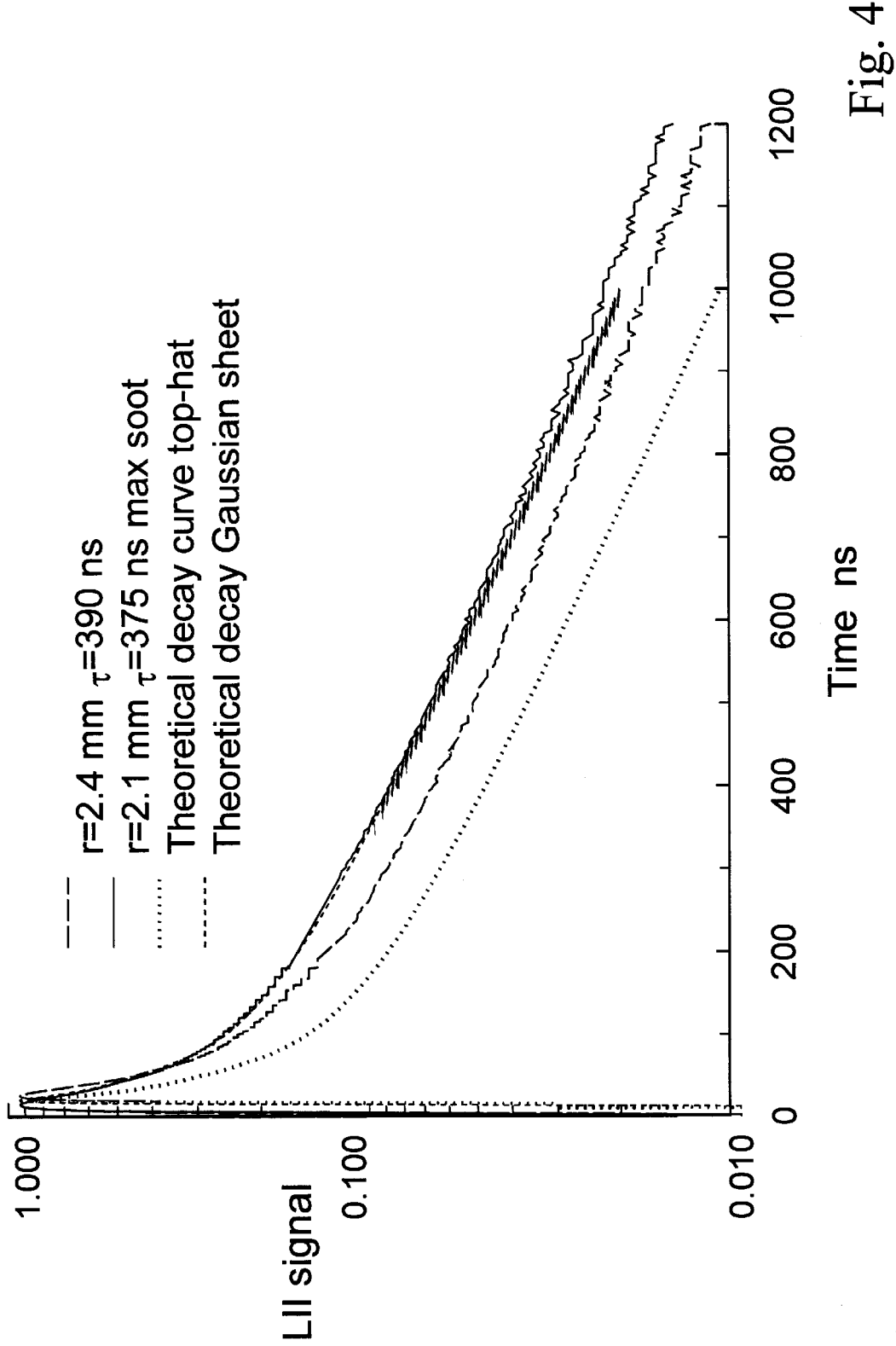
FIG. 4 is a graph of an example of a measured soot decay curves of incandescence light intensity versus time.
Figure 5:
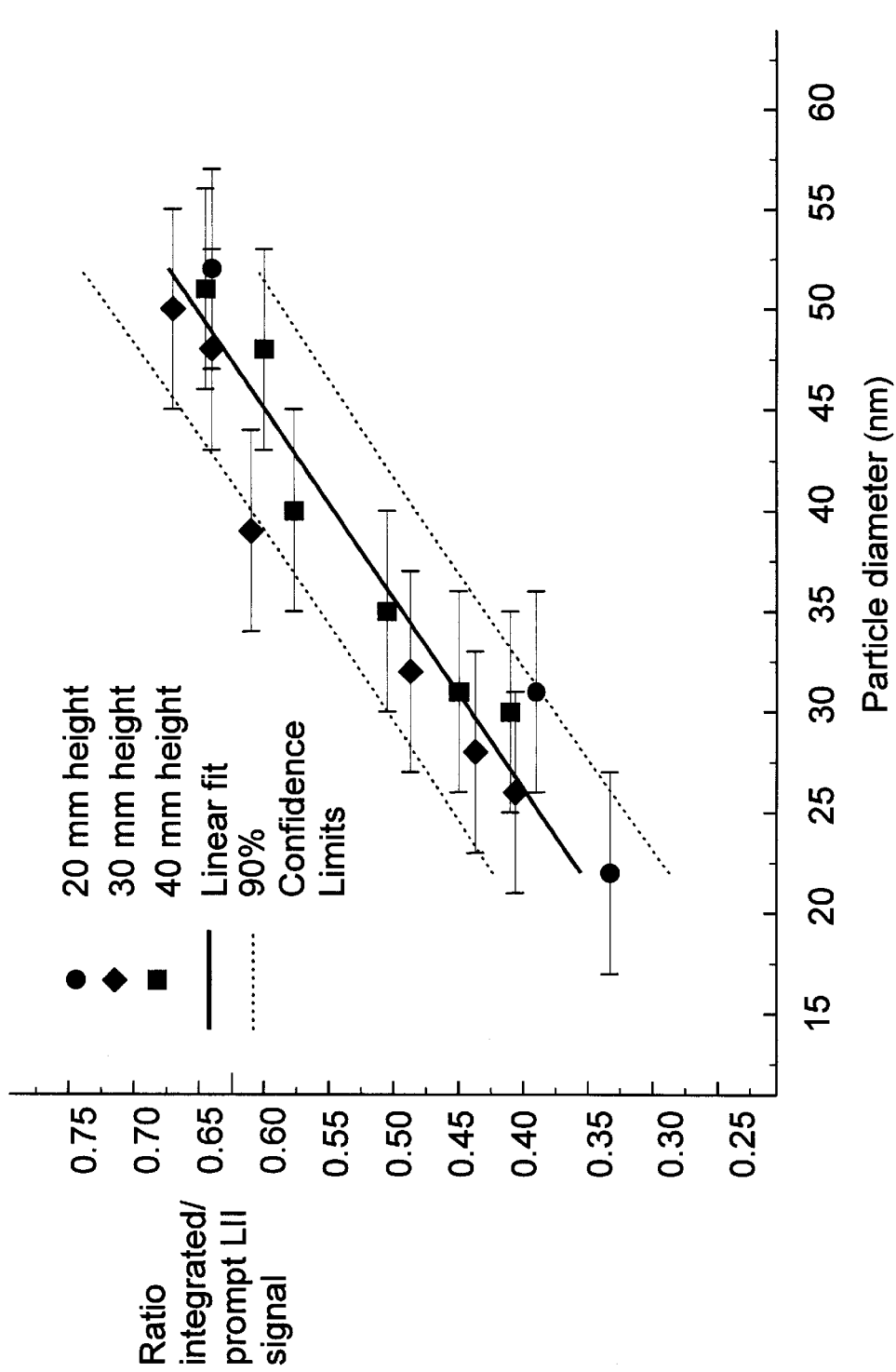
FIG. 5 is a graph of the ratio of integrated to prompt signal versus particle diameter.

FIG. 4 is a graph of an example of the measured incandescence intensity over time illustrating measured and modeled decay curves of two incandescence signals. The ratio of the prompt and integrated signals is a function of the primary particle diameter as can be seen in the graph in FIG. 5 showing the ratio of integrated to prompt signal versus particle diameter. In addition, the incandescence from the prompt signal is proportional to the particulate volume fraction over a wide dynamic range.

The prompt signal is a substantially instantaneous measurement of short enough duration relative to the signal decay time to see little change in the signal. The signal width is controlled through a time gated integrator 40. Better accuracy is achieved if the prompt signal is taken at or close to the peak incandescense, eg. within 10–25 ns of the pulse initiation. However, a later measurement after some cooling has occurred is possible. For greater accuracy, the integrated signal should overlap with the prompt signal. The integrated signal has a duration preferably beginning at the peak intensity and extending at least to a time at which the intensity is less than 10% of the peak intensity, so that a significant portion of the signal has been collected. A typical integration period for the integrated signal is 0.3–1.0 s.

A preferred laser 12 is a Nd:YAG laser operating at its fundamental wavelength of 1064 nm, such as a Surelite 1, manufactured by Continuum Corporation, which advantageously has a short pulse duration. The beam quality in this embodiment is optimized by inserting an aperture of appropriate size in the laser cavity to produce a Gaussian profile in the near and far field. This modification reduces the maximum energy available. Further attenuation of the beam 10 is controlled, by using a half wave plate 14 to rotate the plane of polarization in combination with a vertical polarizer 16 to control the energy delivered to the measurement location. A Pockel cell or other means could be used to automate this function. Of course other lasers can be used, such as a diode laser, a high repetition rate laser or other pulsed lasers, provided energy sufficient to produce measurable incandescence is delivered to the excitation volume, given the wavelength, beam geometry and particulate composition. For soot the energy sufficient to raise particulate temperature to evaporation level is 0.2–0.8 J/cm2. A laser with a short pulse duration, eg. less than about 20 ns, is preferred to minimize particle evaporation during the laser pulse.

The laser light beam expander 18, focusing lens 20 and iris 22 comprise an optical system important for creating a laser sheet at the volume of the measurement location 24 having a Gaussian profile in substantially one plane only. The beam expander 18 broadens the laser light beam, which is then reduced to a thin sheet through the measurement location 24 by the focusing lens 20 or further lens system. The iris 22 is a aperture which prevents scattered light or halo effects from interfering in the measurement location 24. An ideal distribution of laser fluence would be uniform throughout the measurement location 24, but this is difficult to achieve. The excitation volume 24 is preferably a cylindrical shape defined by the intersection of the laser sheet and the diameter of the acceptance angle of signal light gathered by the photodetector 30 by collecting optics such as a collecting lens 26, fiber input 28 or aperture 27. The length of the cylinder is the thickness of the laser sheet. It is particularly difficult to characterize the laser fluence when the intensity varies in all spatial directions. Thus by using only a small part of a sheet of laser light a uniform intensity variation is obtained in two directions and in the third direction, along the axis of viewing, a Gaussian intensity distribution is obtained. For an optical fiber diameter of 0.4 mm, and one to one imaging by the lens 26, only the central 0.4 mm of a 3.6 mm wide sheet is used. This ensures that the laser fluence is approximately constant in a plane perpendicular to the optic axis. There is a Gaussian distribution of fluence along the viewing (optic) axis.

Other measurement volume shapes may be used, as appropriate to different applications. Preferred for high spatial resolution is the relatively small cylinder through the laser sheet, described above. A larger cylindrical full plane sheet can be used to collect more signal data, if spatial resolution is not critical. Alternatively, by altering the angle of the collecting optics 26, 27 or 28, a line of sight volume along the length of the laser light beam can be sampled. It is not necessary to arrange the collecting optics perpendicular to the laser light beam. The laser beam does not have to be reduced through the optical system 18, 20 if a three dimensional volume is sampled. To achieve better spatial resolution in larger sample volumes, a CCD camera can be used to image the distribution of particles during a single laser light pulse.

For maximum accuracy, the beam light intensity profile is measured. Creating a known well defined laser intensity with minimal variation is extremely important since the incandescent signal is highly dependent on the laser energy intensity profile. In the model, energy values for particles other than at the peak intensity are calculated using a uniform distribution of particles about the optical axis aligned with the Gaussian light intensity profile. The particles not located at the peak will receive proportionally less energy, and will produce a different signal as characterized by the spatial profile, which is added cumulatively to determine a total signal for a given time step. A Gaussian profile is not critical as long as the laser fluence over the cross section of the laser beam is characterized. A highly desirable light intensity profile is a "top hat" or square intensity profile of the laser fluence having a constant intensity throughout the laser sheet, but practically this is difficult to achieve.

Conveniently the signal pick up is made with the optical fiber assembly creating a compact and versatile apparatus. The optical fibers 29 provide a more compact assembly, which is no longer dependent on free space optical alignment, allowing more flexibility in positioning detectors. In addition, the single fiber input 28 ensures that the same field of view is delivered to each detector.

FIG. 3 illustrates a bench scale model using a burner 50 having known controlled flame characteristics. This embodiment is constructed in free space without the use of optical fibers or waveguides. FIG. 3 shows the optical detection system in greater detail. Light is divided by the beam splitter 31, the signals are passed through interference filters 38 to select narrow nearly monochromatic wavelength regions. The signals are detected by two or more photomultipliers 32, 34, each controlled by a gated integrator 40 having a set gate width to measure a selected interval. It will be apparent to one skilled in the art that the detectors 32, 34 can be compact photomultipliers, CCD cameras or other photodetectors such as avalanche photodiodes or Gallium Arsenide detectors. The first detector 32 for detecting the prompt signal is connected directly to the gated integrator 40 with a gate width set at 25 ns. The photomultiplier 34 for detecting an integrated signal is connected to a charge-coupled amplifier 42 which measures the total charge collected during the LII signal period (approx. 1000 ns), thus measuring a time integrated signal. The gated integrator 40 connected to the charge coupled amplifier 42, can readily be replaced by a simple sample-and-hold circuit to measure the time integrated signal. The charge coupled amplifier is particularly advantageous for accumulating weak signals, to give a better signal to noise ratio. Alternatively, a single detector, shown in FIG. 9, can be used which records the incandescence signal as a function of time thereby enabling the prompt and integrated signals to be extracted. The incandescence signal is digitized, and the prompt and integrated quantities can be determined numerically from the digitized signal.

For temperature measurement, collection of the incandescent signal is done at at least two separate wavelengths using different wavelength interference filters 38. A narrow wavelength region, typically 20–40 nm, is selected by the filters to obtain two or more essentially monochromatic signals. A first wavelength is selected which shows a change in light intensity due to the elevated temperature. At such high temperatures, the greatest shift is noticeable in wavelengths close to the UV range. A second wavelength is measured such that the relative changes in the intensity/time profiles provides a measure of temperature/time. The ratio of signals at two wavelengths is related to the temperature.

This apparatus has proved effective for measuring particles approximately 10–100 nm in size and concentrations over the range of 0.01–10 ppm. The method can readily be extended to much lower concentrations by increasing the sampled volume and by multiple laser pulse averaging to reduce the LII signal noise.

Figure 6:
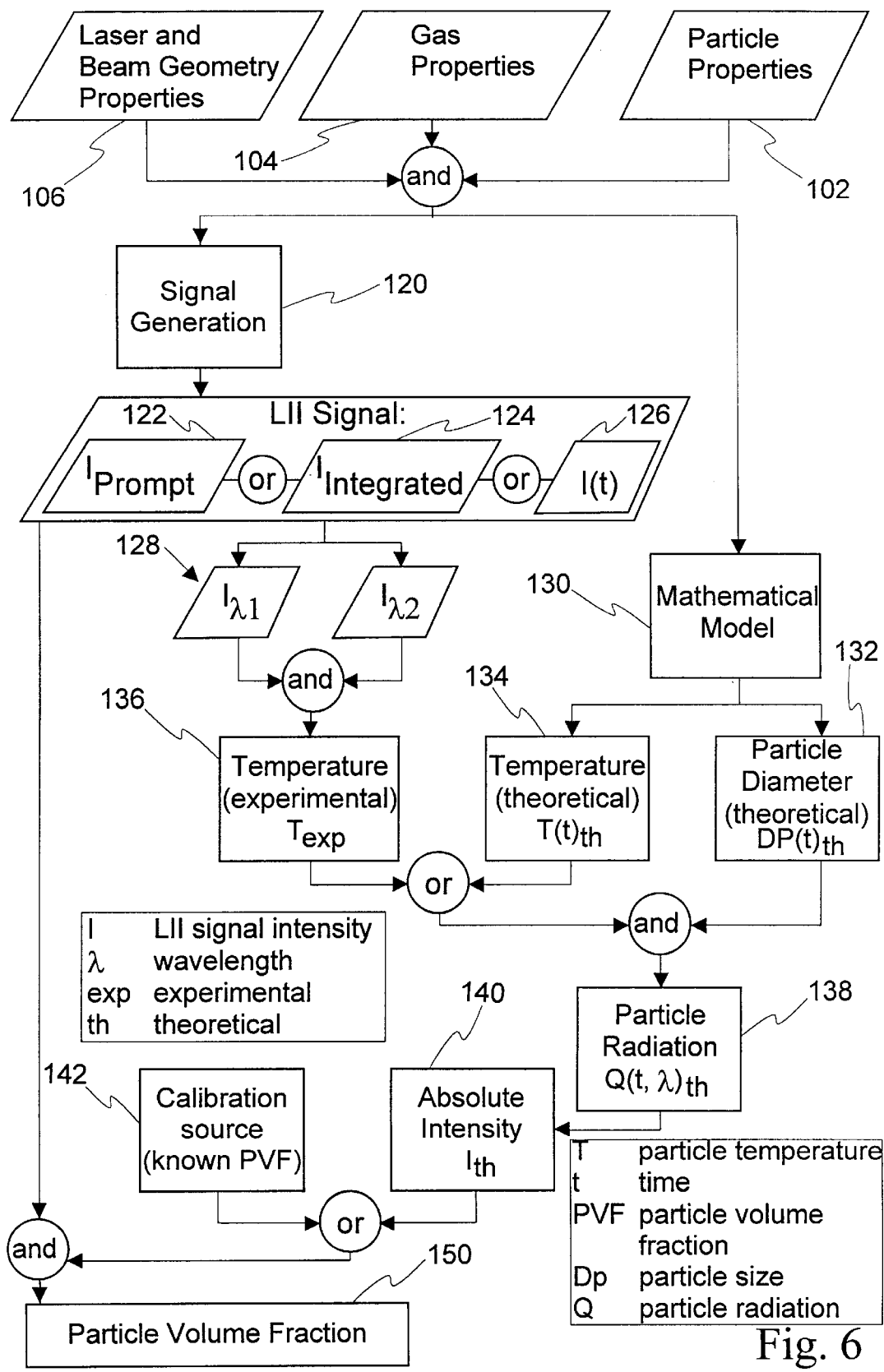
FIG. 6 is a flowchart illustrating the method of determining particle volume fraction.

An outline of the method for determining a particle volume fraction is given in the flowchart shown in FIG. 6. The basic properties of the laser beam 106, the gas 104 and the particle 102 contribute to the signal generation 120 and the mathematical model 130. The signal generation 120 includes a prompt signal 122 and an integrated signal 124. A third signal 126 measures the signal decay over time at a large number of time points. Any of the prompt, integrated or time dependent signal measurements 122, 124, 126 is sufficient in combination with a calibration source 140 to determine the particle volume fraction 150. The prompt signal 122, or its equivalent as determined from the time dependent signal 126, is preferred since it is much less dependent on assumed particle size. The mathematical model 130 combines a theoretical particle diameter 132 based on the input properties 102, 104, 106 with a theoretical temperature 134 also based on the input properties, or with an experimental temperature 136. It is preferred to use an actual experimental temperature. Experimental temperature 136 is determined by sampling the signal 122, 124 or 126 with two or more different wavelengths 128 which provide incandescence intensity signatures indicative of temperature. Temperature information 134 or 136 is combined with particle diameter to predict a net particle radiation to the surrounding gas 138. This value can be used to provide an absolute light intensity calibration of the system 140. Alternatively, traditional methods 142 may be used to calibrate with a source of known particle volume fraction. This calibrated radiation is used to determine a volume fraction measurement 150 of the prompt, integrated or time dependent signal 122, 124, 126.

Figure 7:
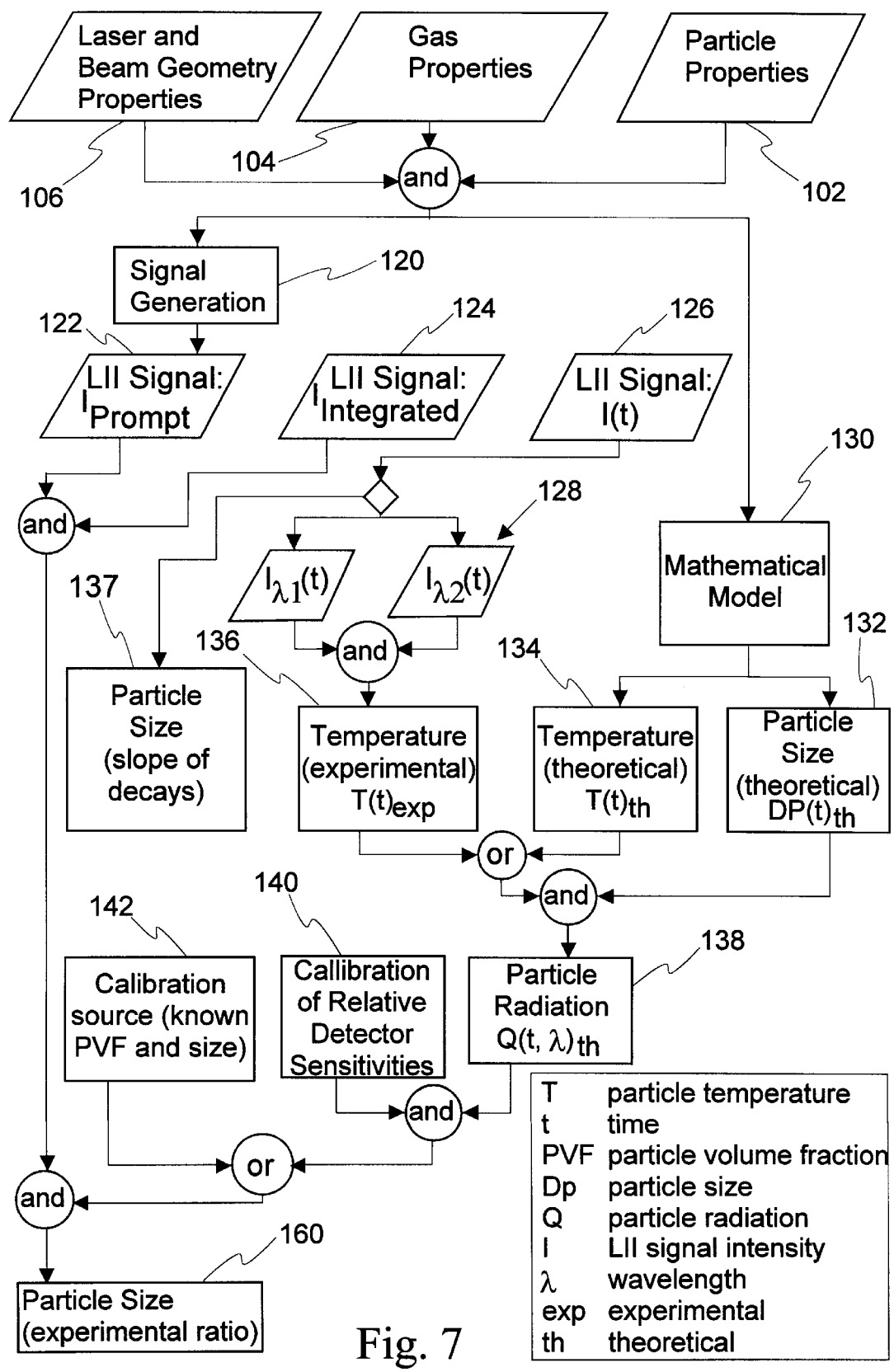
FIG. 7 is a flowchart illustrating the method of determining particle size.

Modification of the method to determine particle sizing is readily apparent from the outline shown in FIG. 7. In this case the prompt signal 122 and integrated signal 124 are combined as a ratio which is a function of particle size determined from a calibrated net radiation 138 and 140, or from a traditional calibration source of known volume fraction and size 142, to quantify the particle size 160.

For quantitative measurements of volume fraction calibration of the detectors is necessary. This can be accomplished, for example, by first measuring a laminar diffusion of a flame with a known soot concentration, or through other traditional methods of concentration measurement for a known concentration. For example, by dispersing carbon particles in a liquid with known mass concentration, drying the liquid and measuring the residual particle volume. Alternatively, an extended source of known radiance, such as a strip filament lamp, the source being larger than the sample cross section, whose brightness temperature is known, can be used as the source for the LII detection system to provide an absolute intensity calibration. The absolute intensity calibrates the sensitivity of the photodetectors 32, 34. Once a calibration factor is determined, the device can be used, for example in situ without further calibration. The signal measured can then be combined with the calibration factor to calculate particle concentration. Errors associated with uncertainties in the filter characteristics, lens collection efficiency, aperture size, and optical system magnification are shown to be largely eliminated using this calibration procedure. Advantageously the use of the same optical components for calibration and concentration measurement eliminates potential errors.

The particle concentration is determined by measuring the absolute LII signal, and comparing that to the calculated light radiation per particle to calculate the concentration of particles. The light radiation per particle is calculated from the particle diameter and the particle temperature. A small sized particle diameter can be approximated without compromising the accuracy of the concentration calculation. The particle temperature can be determined either by measuring an experimental temperature or using the mathematical model to predict the temperature. An extended source of known radiance (power/unit area of source-steradians-wavelength interval) whose brightness temperature is known is used to calibrate the detection system. In a preferred embodiment a strip filament is used as the extended source of known radiance. The source light signal is measured by the photodetectors of the LII system. A true temperature is obtained from the source light signal measured by the photodetectors and the known brightness temperature of the source. A radiance is obtained at a predetermined wavelength from an emissivity of the source as a function of temperature and wavelength. The calibrated radiation source signal is determined by the spectral radiance of the lamp, i.e. the light power emitted per unit area, per unit solid angle, and per unit wavelength interval and is given by equation (1):

$$R_S(\lambda) = \frac{2c^2 h \varepsilon(\lambda, T)}{\lambda^5}\left[e^{\frac{hc}{k\lambda T}} - 1\right]^{-1} = \frac{C_1 \varepsilon(\lambda, T)}{\lambda^5}\left[e^{\frac{C_2}{\lambda T}} - 1\right]^{-1} \quad (1)$$

wherein the first and second radiation constants are: $C_1 = 3.74177 \times 10^{-16}$ w m$^{-3}$ and $C_2 = 0.014388$ m K and $\varepsilon(\lambda, T)$ is the emissivity as a function of wavelength and temperature. The source light signal and the radiance are used to determine a calibration factor for calibrating the photodetectors.

Figure 10:
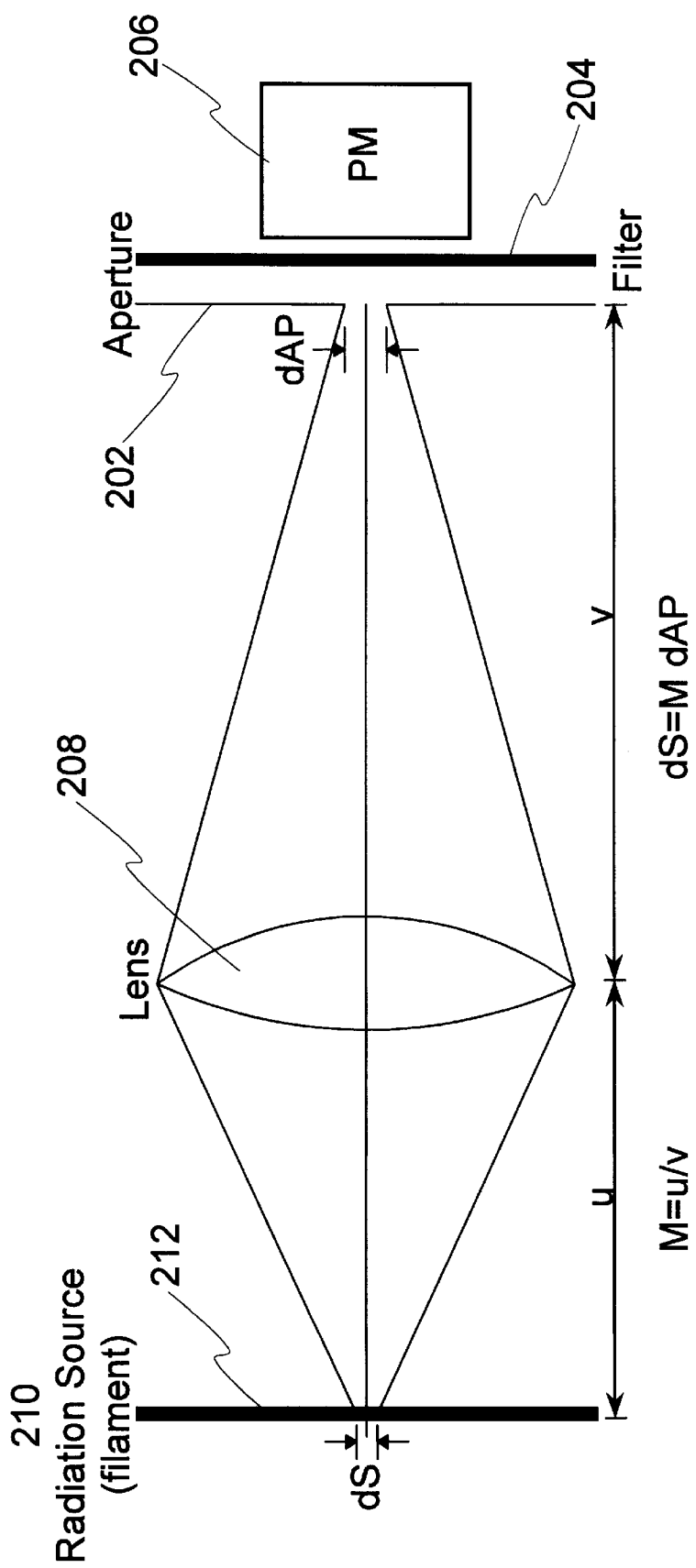

The optical schematic for the absolute light intensity calibration of the extended source of known radiance signal is shown in FIG. 10. In an embodiment of the invention an aperture 202 having a diameter of 1.04 mm is placed in front of a filter 204 and a photomultiplier (PM) 206. This aperture 202 is imaged with a lens 208 onto a radiation source 210. In an embodiment of the invention the radiation source 210 is a strip filament lamp and the aperture 202 is imaged onto the filament 212 of a calibrated strip filament lamp but other extended sources of known spectral radiance, e.g. a blackbody calibration source, can be used for this purpose. Furthermore, in an embodiment of the invention the lens has a focal length of 190 mm, a diameter of 54 mm, and a magnification of M=0.5. The magnification of the lens is determined from the distance u, i.e. the distance between the filament and the lens, and the distance v, i.e. the distance between the lens and the aperture, and equals M=u/v. The calibrated lamp is placed so that its filament is coincident with an LII signal generation region. The lamp, whose filament is 3×8 mm in an embodiment of the invention, has a known brightness temperature, at 654 nm, as a function of lamp current.

Calibrating absolute intensities in LII systems requires a knowledge of the particle temperature either from a numerical model of particulate heating or experimental observation of the particulate temperature. Further, by using a known particle temperature a particle volume fraction is calculated. This avoids the need for a calibration using a source of particulates with a known particle volume fraction resulting in a calibration independent method and apparatus for measuring particle volume fraction or particle concentrations. Thus, the method and the apparatus in accordance with the present invention incorporating absolute intensity calibration do not require a source of known particulate concentration for calibration purposes.

This prepares the basis for providing portable LII instruments which may be particularly useful for applications of measuring exhaust particulate, measurements in engine test cells in laboratories, emissions compliance measurements and road-side checks, for applications of stack particulate measurements in furnaces and boilers, for airborne particulate monitoring, and for on-line process monitoring.

For absolute intensity measurements the particle temperature is needed, which is obtained either from the model or from LII signal measurements at at least two different light wavelengths. For particles of known emissivity the particle temperature is proportional to the ratio of the LII signal intensity of the two measurements at different wavelengths. If the model is used to predict the particle temperature then a knowledge of the type of particle and its properties is needed as described in the flow chart of FIG. 8.

One implementation of the particle size measurement technique in accordance with the invention is also dependent on the mathematical model which maps a temperature history of the particles, from their peak incandescence and examining the decay rates. The model in accordance with the present invention better describes the decay curve of cooling for soot particles than seen in the prior art, therefore providing more accurate particle size interpretation. The model assumes a uniform distribution of particles within the measurement volume and incorporates the profile of the laser light intensity, compensating for less energy received by particles not at the peak of the intensity profile. Additional characteristics of the present model have greatly improved the accuracy of measurements, such as: the use of temperature dependent gas and particle properties; modeling the true profile of the laser light intensity in space and time; the use of measured particle properties, instead of assumed values from the literature; and wavelength dependent filter transmission data rather than broad band sample collection.

Figure 8:
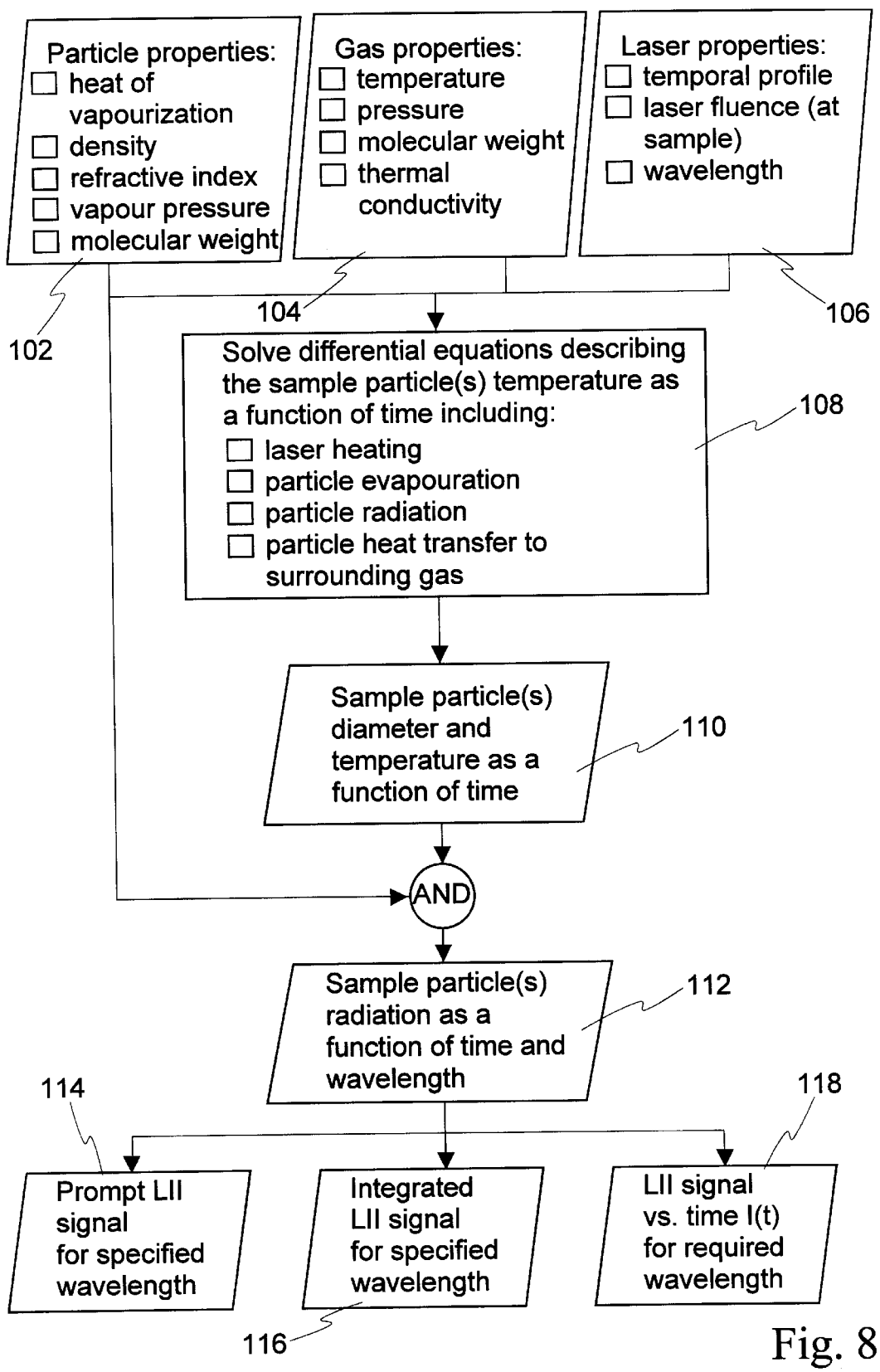
FIG. 8 is a flowchart illustrating the mathematical model process.

FIG. 8 is a flowchart outlining the modeling process. The model is optimized for soot particles, but is generally applicable to any particle which absorbs laser light energy with an evaporation temperature sufficiently high to produce measurable incandescence, and may be applied to other particles such as alumina, silica, and titania and many other metals and metal oxides. The model considers soot agglomerates to be made up of uniform, non-overlapping primary spherical particles. The agglomerate volume is then found by multiplying the volume of a single primary particle by Np, the number of primary particles within the agglomerate. First the physical properties of the particle, the gas and the laser are considered as outlined in blocks 102, 104 and 106 respectively. Particle properties 102 include heat of vaporization; density; refractive index; vapor pressure; and molecular weight. Gas properties 104 include temperature; pressure; molecular weight; and thermal conductivity. The laser properties 106 include temporal profile; laser fluence spatial profile at sample; and wavelength. These properties are incorporated to solve the differential equations describing the sample particle temperature and diameter as a function of time outlined in block 108. These equations include laser heating; particle evaporation; particle radiation; and particle heat transfer to the surrounding gas. These equations enable the determination of the sample particle diameter and temperature as a function of time indicated in block 110. Together with the particle properties 102, the sample particle diameter and temperature as a function of time 110, the sample particle radiation as a function of time and wavelength 112 is predicted for the prompt LII signal at an arbitrary specified wavelength 114, the integrated LII signal at an arbitrary specified wavelength 116, and a sample providing a decay curve of signal vs. time l(t) for an arbitrary wavelength 118.

The heat transfer energy balance equation is:

$$C_a q - \frac{2k_a(T-T_0)\pi D^2}{(D+G\lambda_{MFP})} + \frac{\Delta H_v}{M_v}\frac{dM}{dt} + q_{rad} - \frac{1}{6}\pi D^3 \rho_s c_s \frac{\partial T}{\partial t} = 0$$

The equation includes the absorbed laser light energy assuming soot particles are agglomerates of non-overlapping spheres made up of primary particles and that primary particles are in the Rayleigh limit. The equation further includes heat transfer to the surrounding gas, the evaporation of the material, the net particle radiation to the surroundings, and finally the particle heating.

A glossary of terms to the equation follows:

| | |
|---|---|
| $C_a$ | particle optical absorption cross section (m$^2$) |
| $C_S$ | specific heat of particle |
| $d_P$ | primary particle diameter |
| G | geometry dependent heat transfer factor G = 8f/($\alpha(\gamma + 1)$) |
| $\Delta H_v$ | heat of vaporisation of particle |
| $k_a$ | thermal conductivity of ambient gas |
| $M_v$ | molecular weight particle vapor |
| M | molecular mass of particle |
| q | laser intensity |
| T | particle surface temperature |
| $T_0$ | ambient gas temperature |
| $\lambda_{MFP}$ | the mean free path |
| | $\lambda_{MFP} = 1/(2^{0.5}\pi(\sigma_{AB})2$ in rigid sphere approximation (m). |
| $\rho_S$ | density of particle (kg/m$^3$) |

A further preferred apparatus in accordance with the invention is shown in FIG. 9. FIG. 9 shows an alternative embodiment similar to the embodiment shown in FIG. 2, having a single photodetector 35, which is connected to a transient digitizer 37 to measure the complete incandescence signal. A single narrow wavelength band is collected. The particle temperature for the determination of volume fraction is then determined from the mathematical model. The prompt and integrated signals are obtained from the transient digitizer 37 to obtain particle size and volume fraction. Advantageously, this economical system when used with an absolute light intensity calibration provides particle size measurement and particle volume fraction measurements in a compact and practical arrangement.

Of course, numerous other embodiments of the apparatus and method may be envisaged, without departing from the spirit and scope of the invention as defined in the appended claims.

What is claimed is:

1. A method for determining an average particle size of one or more particles in a defined volume of gas comprising the steps of:
   exposing the volume of gas to a laser light beam pulse to cause the one or more particles to incandesce;
   obtaining a measurement of a prompt signal of incandescence intensity within a period of substantially unchanged intensity after the laser pulse with a photodetector means;
   obtaining a measurement of a time integrated signal of incandescence intensity over a duration of time after the laser pulse with a photodetector means;
   calculating a ratio of the prompt and integrated signals for application to a mathematical model representing a heating and cooling of the one or more particles and the type of particle; and
   determining the average particle size in dependence upon the ratio and the model.

2. A method as defined in claim 1, wherein the time integrated signal is detected over a duration comprising a major portion of a total incandescence intensity.

3. A method as defined in claim 2, wherein the time integrated signal is detected over a duration from a time at substantially a peak incandescence intensity to a time at which an intensity is less than 10% of the peak intensity.

4. A method as defined in claim 2, wherein the prompt signal is detected substantially at a peak incandescence intensity.

5. A method as defined in claim 4, wherein the prompt signal overlaps simultaneously with the time integrated signal.

6. A method as defined in claim 5, wherein the laser beam pulse is optimized to have a controlled spatial profile in a near field and a far field.

7. A method as defined in claim 6 wherein the laser beam pulse is focused to form a laser sheet through the defined volume of gas.

8. A method as defined in claim 1, further including a method of simultaneously determining a particle volume fraction within the defined volume comprising the additional steps of:

incorporating the measurement of one of the prompt signal and of the time integrated signal and a time dependent signal of incandescence intensity into the mathematical model representing a heating and cooling of the one or more particles and the type of particle;

performing a calibration of a signal intensity to quantify the measurement; and calculating the particle volume fraction from the calibration and the measurement.

9. A method as defined in claim 8, wherein the model estimates a theoretical particle temperature and a theoretical particle diameter based on an input of particle properties, gas properties and laser properties.

10. A method as defined in claim 8, further including measuring a particle temperature wherein the model estimates a theoretical particle diameter and incorporates the measured temperature.

11. A method as defined in claim 8 wherein calibration comprises calibrating the photodetector means to quantify the sensitivity of the photodetector means to provide an absolute intensity calibration comprising the additional steps of:

(a) providing an extended source of known radiance with a known brightness temperature for calibrating the detector means prior to exposing the volume to a laser beam pulse, the source being disposed in the defined volume;

(b) measuring a signal from the source on the photodetector means;

(c) obtaining a true temperature for the signal measured in step (b) from the known brightness temperature of the source and the emissivity of the source;

(d) obtaining a radiance from an emissivity of the source as a function of temperature and wavelength; the radiance being obtained at a predetermined wavelength and (e) determining a calibration factor for calibrating the photodetector means from the signal measured in step (b) and the radiance of step (d).

12. An apparatus for determining an average particle size of one or more particles in a defined volume of gas in a laser induced incandescence system comprising:

a laser for generating a pulsed light beam into the defined volume of gas for causing the one or more particles to incandesce;

at least one photodetector for detecting a prompt signal within a period of substantially unchanged incandescence intensity and for detecting a time integrated signal over a duration of time including a major portion of a total incandescence intensity;

processing means for calculating a ratio of the prompt signal and the time integrated signal and applying the ratio to a mathematical model representing a heating and cooling of the one or more particles and the type of particle to determine the average particle size.

13. An apparatus as defined in claim 12, including collecting optics for directing the incandescence caused to the at least one detector wherein the defined volume comprises an intersection of a collection diameter determined by the collecting optics and the pulsed beam.

14. An apparatus as defined in claim 13, wherein the collecting optics includes at least one filter for filtering the incandescence signal to at least one selected narrow wavelength band before directing a filtered incandescence signal to the at least one detector.

15. An apparatus as defined in claim 14, wherein the at least one detector comprises a single photodetector and a transient digitizer for detecting the prompt signal and the time integrated signal.

16. An apparatus as defined in claim 15, wherein the collecting optics further includes optical fiber for conducting the incandescence signals to the single photodetector.

17. An apparatus as defined in claim 13, further including a first detector for measuring the prompt signal and a second detector for measuring the time integrated signal.

18. An apparatus as defined in claim 17, wherein the collecting optics further includes optical fibers for conducting the incandescence signals to the first and second detectors.

19. An apparatus as defined in claim 17, wherein the collecting optics include an optical splitter for dividing the incandescence signal between the first detector and the second detector.

20. An apparatus as defined in claim 19, further including optical elements for optimizing the pulsed laser beam to pass through the defined volume having a controlled spatial profile in a near field and a far field.

21. An apparatus as defined in claim 20, wherein the optical elements include a beam expander, and a focusing lens system, to form a laser sheet having a substantially flat spatial profile in two orthogonal planes and a known variance in an optic axis.

22. An apparatus as defined in claim 20, wherein the collecting optics are disposed substantially perpendicular to the laser sheet.

23. An apparatus as defined in claim 12 further including calibration means adapted for quantifying a particle volume fraction measurement.

24. An apparatus as defined in claim 23, wherein the calibration means comprises an extended source of known radiance having a known brightness temperature for calibrating the at least one photodetector to quantify the sensitivity of the at least one photodetector.

25. An apparatus as defined in claim 23, including at least two filters associated with the at least one detector for filtering the incandescence signals at at least two different wavelengths for the determination of particle temperature.

* * * * *